United States Patent [19]

Pizzol et al.

[11] Patent Number: 4,765,274
[45] Date of Patent: Aug. 23, 1988

[54] METHOD OF MASS PRODUCING AN ENTOMOPHAGOUS INSECT

[75] Inventors: Jeannine Pizzol, Juan-Les-Ping; Jean Voegele; Pierre Jourdheuil, both of Antibes; Bernard Raynaud, Champigny-sur-Marne; Yves Miermont, Avignon, all of France

[73] Assignees: Societe Cooperative Agricole de Semences de Limagne "Limagrain", Chappes; Union Nationale des Cooperatives Agricoles d'Approvisionnement; Institut National de la Recherche Agronomique, both of Paris, all of France

[21] Appl. No.: 894,495

[22] Filed: Aug. 4, 1986

[30] Foreign Application Priority Data

Aug. 7, 1985 [FR] France .................. 85 12115

[51] Int. Cl.[4] ............................................. A01K 67/00
[52] U.S. Cl. .......................................... 119/15; 119/1
[58] Field of Search .............................. 119/15, 1; 6/1

[56] References Cited

U.S. PATENT DOCUMENTS

| 2,539,633 | 1/1951 | Morrill | 119/1 |
| 3,847,113 | 11/1974 | Andreev et al. | 119/1 X |
| 3,893,420 | 7/1975 | Andreev et al. | 119/1 |
| 3,941,089 | 3/1976 | Andreev et al. | 119/15 X |
| 4,207,637 | 6/1980 | Niebur | 6/1 |
| 4,370,946 | 2/1983 | Voegelé et al. | 119/15 X |
| 4,411,220 | 10/1983 | Voegelé et al. | 119/15 X |
| 4,646,883 | 3/1987 | Maedgen, Jr. | 119/15 X |

Primary Examiner—David A. Scherbel
Assistant Examiner—Richard E. Chilcot, Jr.
Attorney, Agent, or Firm—Browdy and Neimark

[57] ABSTRACT

The invention relates to a method for the mass production of an entomophagous insect such as *Trichogramma maidis* insect from a substitution host such as the egg of the meal moth *Ephestia kuehniella*, as well as a device for implementation of this method and the application of the method to the biological fight against maize crop ravagers.

7 Claims, 3 Drawing Sheets

METHOD OF MASS PRODUCING AN ENTOMOPHAGOUS INSECT

BACKGROUND OF THE INVENTION

1. Field of the Invention

The invention relates generally to the multiplication and mass production of an entomophagous insect such as *Trichogramma maidis*, from a substitution host such as the egg of the meal moth *Ephestia kuehniella*, said entomophagous being in this case released in seasonal inundatory batches in the biological fight against a maize crop ravager, Ostrinia nubilalis or maize meal moth.

The invention relates then more particuiary to a method for the mass production of an entomophagous insect with a device for implementation thereof, as well as the application of said method to the biological struggle using microcontainers intended for in the field release.

2. Description of the Prior Art

In the case of Trichogrammides, the production of this entomophagous insect has been achieved up to now in so called "multiplication" cages where host eggs are presented in a monolayer on plates to a quantity of adult Trichogrammides, or inoculum, in a ratio of 10/1 and previously emerged from parasitized eggs disposed loose in the cage.

When it is necessary to provide cold storage before using the parasitized eggs, the duration of the parasitism of the host eggs by inoculum of Trichogrammides must be limited to 48 hours at 25° C. (compare work of Madame PIZZOL on the induction of the diapause in *Trichogramma maidis* allowing this cold storage). On average, 75% of the host eggs thus presented are parasitized. A part of the eggs thus parasitized is however recyled as inoculum for the next generation.

This method of multiplication in cages for 24 to 48 hours has certain drawbacks:

1° Handling of numerous cages without great possibility of automation;

2° Partial use of the laying potential of the Trichogrammide females, the parasitism being at most 48 hours at 25° C., minimum condition indispensable for a correct rate of induction of diapause of the *Trichogrammide lavae* before cold storage.

The parasitism time of the part recycled as inoculum must not exceed 48 hours either so as to avoid too great a staggering of the emergences in the cages. Even in this case, it is then necessary to wait for at least 48 hours after the first emergences of the inoculum so as to introduce the tray of host eggs.

The present invention aims then at overcoming these drawbacks, by providing a method of multiplication and mass production of entomophagous insects by formation of host eggs parasitized in a population cage, finding an advantageous application in the case of Trichogrammides and in the biological fight against the maize meal moth.

SUMMARY OF THE INVENTION

In accordance with the method of the invention, a constant population is kept in the cage of adult entomorphagous insects from an inoculum formed of first parasitized host eggs having undergone an appropriate previous incubation, said inoculum is activated in the cage, second host eggs are continuously presented for 24 hours to be parasitized by the entomorphagous insects emerged from said inoculum, the second host eggs thus parasitized are continuously collected with a view to their subsequent conditioning treatment and a fraction there-of is taken off so as to form said inoculum after the incubation.

After collecting the second parasitized host eggs, they are applied as inoculum in the presence of healthy eggs of the entomophagous insects, in the form of a proportioned mixtured introduced into microcontainers for release in the field and treated as a function of the desired emergence spread of the entomophagous insects.

For implementing the method such as defined above, the device is essentially formed by a temperature regulated enclosure forming a population cage, having a first transporting belt for the inoculum and a second transporting belt for the host eggs to be parasitized, guided on rollers and driven at the same speed by a motor unit, said cage being associated with external members for recovering the parasitized host eggs and for reconditioning said second belt, and comprising means for forming, supporting and introducing the inoculum after its incubation, whereby the device operates automatically and continuously with a minimum manual intervention for a high production and of homogeneous quality.

BRIEF DESCRIPTION OF THE DRAWINGS

Other features and advantages of the invention will be clear from the following description, with reference to the accompanying drawings in which.

In these drawings, the same references designate the same elements.

DESCRIPTION OF THE PREFERRED EMBODIMENT

In the case for example of trichogrammides, a population of said trichogrammides, constant with respect to its quantity and its biological potentialities, is kept in a cage and the host eggs are brought continuously and regularily with a view to their parasitization. For this, a regular supply of trichogrammides offsetting the death rate is required and supplied by the cage itself, in the form of first parasited host eggs incubated for two weeks at 22° C., introduced into a housing provided for this purpose on the cage where the trichogrammides will be able to emerge and parasitize the second host eggs which are continuously presented to them. Advantageously, the stay time of the inoculum in the cage is five days and that of the second host eggs is 24 hours, as will be better explained hereafter.

Figure 1:
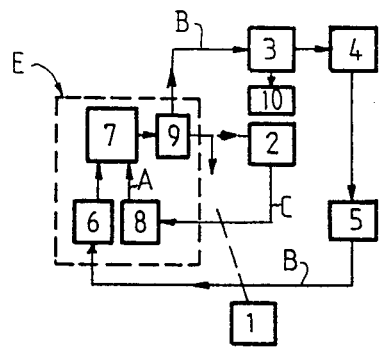
FIG. 1 shows a block diagram of the device of the invention, illustrating the method.
Figure 2:
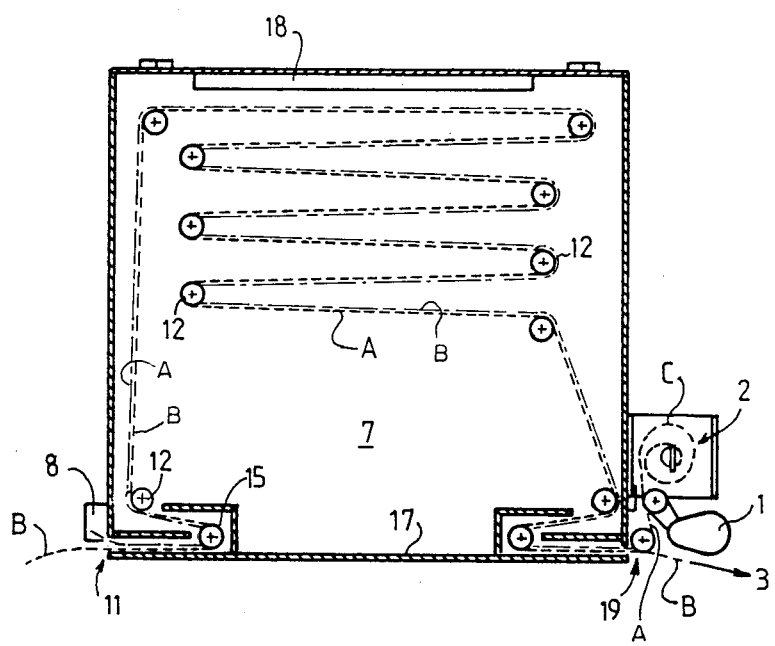
FIG. 2 shows a schematical view of the front of the population cage.
Figure 3:
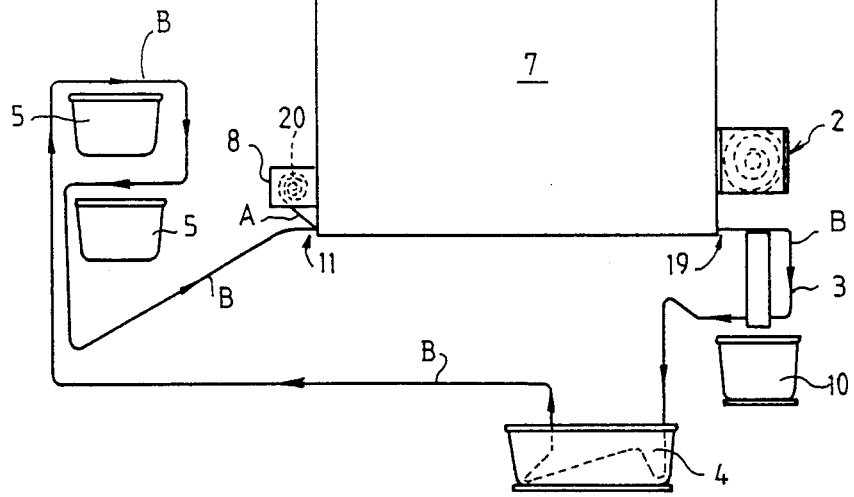
FIG. 3 shows a schematical view of the general overall layout of the production device.
Figure 4:
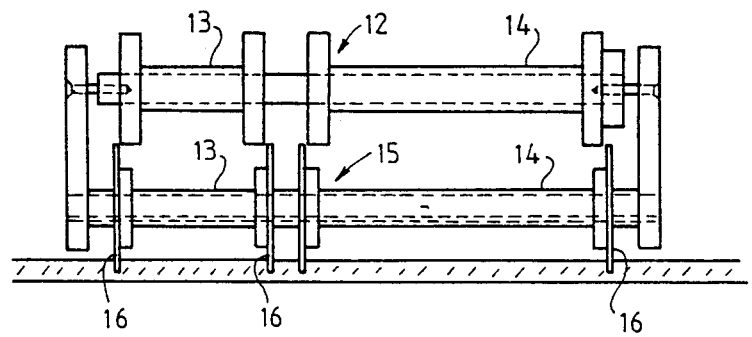
FIG. 4 shows an enlarged schematical view of a detail of the rollers guiding the transporting belts.

Referring to FIG. 1, the device for implementing the above method comprises different stations with respect to the unit of general reference E comprising the cage properly speaking 7 in which two transporting belts A and B travel continuously, respectively narrow for the first host eggs forming the cage inoculum and wide with a double face for the second host eggs, both driven at a suitable speed by a motor unit 1.

At the output of the population cage 7, the narrow belt C supporting eggs which have just been parasitized and are intended for forming the cage inoculum is wound by means of a drive motor 1 into a roll of general reference 2.

For activating this cage inoculum, after incubation, the rolls are introduced at 8 into the cage, in a housing where five rolls 2 are held. The introduction of a roll 2 at 8 causes a roll 2 to be expelled from the cage at 9. A roll 2 remains then five days in the cage, which is suitable for complete emergence of the trichogrammides from the first host eggs.

At the outlet of the population cage 7, the wide belt B supporting the second parasitized host eggs by gumming is brushed by brush 21 at 3 on both faces, the eggs being recovered at 10 in the form of a powder for their subsequent treatment. Once brushed, belt B is cleaned at 4, rinsed, then again gummed at glue applying station 20 and provided with healthy host eggs on both faces at 5 before reintroduction thereof at 6 into cage 7. The travel time between stations 3 and 6 external to cage 7 also lasts 24 hours.

Referring to FIGS. 1 to 4, cage 7 is formed by an enclosure having an inlet 11 representing the two stations 6 and 8, respectively for belt B and for belt A. These two belts are guided over coaxial rollers 12, one for belt A (13) and the other for belt B (14). The first roller 15 of inlet 11 is advantageously provided with the usual brake 16 for adjusting the tension of the belts. The cage further comprises a removable bottom 17, intended more particularly for removing the dead trichogrammides. Moreover, an appropriate light source 18 is disposed on the upper internal face of cage 7 so as to maintain the essential part of the trichogrammide population towards the top of the cage, whereas these latter are fed for example with honey which may be disposed either automatically on the edge of the belts or manually at the level of said upper internal face.

As mentioned above, belts A and B are driven by motor unit 1, at a speed such that these belts travel over their paths at the same speed between the inlet 11 and the outlet 19 of the cage within 24 hours. At the outlet 19, belt A is extracted, while a new belt of parasited eggs which have been subjected to incubation in a separate station (not shown) is introduced in the form of a roll 20 in station 8. Belt B is directed over a brush roller 3 from which the second parasitized host eggs are collected in the form of a powder in a receptacle 10. Belt B is then rinsed in a bath 4, regummed at 5 on both its faces and provided with healthy host eggs, then introduced into the cage through inlet 11. Belt A, coming from the incubation post, introduced in the form of a roll 20 in one of the housings 8 of cage 7, advances for activation thereof at a speed such that it covers its total travel path in five days, which time corresponds to the time required for the emergence of the trichogrammides.

In accordance with the present invention, the host eggs collected in the container 10 of the production device are then applied as inoculum placed in the presence of third healthy host eggs in microcontainers, each in the form for example of a cardboard capsule of 1.2 cm in diameter in the form of two half spheres bonded then subsequently pierced for release in the field.

The principle consists in having the host eggs parasitized directly in this capsule by associating therewith the appropriate capsule inoculum. This is calculated so that the number of parasitized eggs is maximum while limiting superparasitization to an acceptable threshold. In the case of the capsules, the ratio between parasitized "black" eggs, (inoculum) and "white" eggs to be parasitized is 1/15.

Depending on whether the emergence of the adults is grouped or staggered, in the first case we have the possibility of parasitizing with a given inoculum the largest number of host eggs in a short time, whereas in the second case, the period of action of the trichogrammides in the field is extended.

Grouping together of the emergences is moreover indispensable in the case of cold conditioning of the development of the trichogrammides for inducing a diapause allowing a long period of storage of the biological product, in the way described in the French Pat. No. 79 17 774. So as to define the optimum conditions for treating and loading the capsules, the batches of parasitized eggs, from which the very first adult appeared, are subjected to relatively low temperatures (10°, 14° and 18° C. and for times of 24 to 48 hours) so as to retard the nymphal development and group together the emergence of the adults. After this cold treatment, these batches are exposed to high temperatures (22° to 25° C.) with checks morning and evening of the emergences during three days (so as to obtain emergences of the adult trichogrammides in a short space of time. A reference batch has moreover been subjected to development at a constant temperature of 22° C.

The groups appearing in table 1 below show that it is the inoculums exposed to 10° and 14° C. for 24 hours to 48 hours and subjected to a passage at 25° C. for 15 hours, which offer the optimum emergence conditions (<90%).

Figure 5:
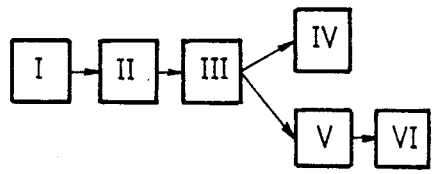
FIG. 5 shows a block diagram of the capsule parasitism method.

Consequently and in practice the host eggs to be parasitized as well as the inoculum are introduced into the capsules. These capsules, once closed, are exposed to 10° to 14° C. for 24 to 48 hours before being subjected to 25° C. for a period of 15 hours. After this stay time at 25° C. two types of development may be obtained: a continuous development by subjecting the capsules to 22°–25° C. until the death of the trichogrammides, or stopping development called diapause by subjecting the capsules only 24 to 36 hours at 22°–25° C. and then exposing them for 40 days at 14° C. then three to twelve months at 3° C. The different phases of treatment are given in the block diagram of FIG. 5, namely:

I: Putting into capsules—Inoculum with first emerged adult + *Ephestia kuehniella* host eggs to be parasitized.
II: Slowing down of development by cooling: 10°–14° C. for 24 to 48 hours.
III: Heating for grouping together the emergence of the adults: 25° C., 15 hours.
IV: Continuous development: 22° or 25° C.
V: Development at 22° or 25° C., 24 to 36 hours.
VI: Diapause—induction for 40 days at 14° C.; storage three to twelve months at 30° C.

TABLE 1 rate of emergence before or after heating at 25° C. and 22° C.
as a function of exposure times of 24 and 48 hours to temperatures close to the development threshold

| Cold treatment | | Emergence rate before heating | Emergence rate after heating at 25° C. | | | | | |
|---|---|---|---|---|---|---|---|---|
| | | | 1st day | | 2nd day | | 3rd day | |
| Temp | Time | | morning | evening | morning | evening | morning | evening |
| 10° C. | 24 H | 2% to 8% | >90% | | | >90% | | |
| | 48 H | | | | | | | |
| 14° C. | 24 H | | | | | | | |
| | 48 H | | | | | | | |
| 18° C. | 24 H | 30% to 41% | | | | | | |
| | 48 H | | | | | | | |
| Control 22° C. | | | 6.2% | | 16.8% | | 86% | |

| Cold treatment | | Emergence rate before reactivation | Emergence rate after heating at 22° C. | | | | | |
|---|---|---|---|---|---|---|---|---|
| | | | 1st day | | 2nd day | | 3rd day | |
| Temp | Time | | morning | evening | morning | evening | morning | evening |
| 10° C. | 24 H | 2% to 8% | ≦90% | | | >90% | | |
| | 48 H | | | | | | | |
| 14° C. | 24 H | | <80% | | | | | |
| | 48 H | | | | | | | |
| 18° C. | 24 H | 30% to 41% | ≦80% | | | | | |
| | 48 H | | | | | | | |

Figure 6:
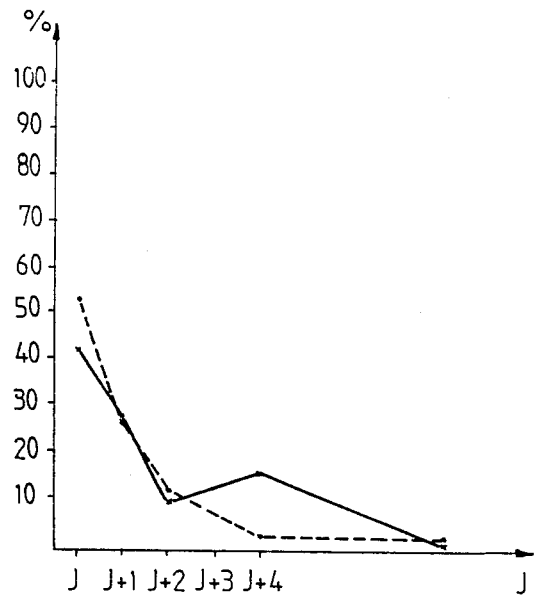
FIGS. 6 and 7 show graphs illustrating the spread of the emergences during release, as a function of the parasitism method.

The spread of hatching of the progeniture from this inoculum was followed both for the continuous development and development after storage at 3° for three months. The results are given in the graphs of FIGS. 6 and 7 where the spread of emergences in days is plotted as abscissa and as ordinates the percentage of emerged adults. In these graphs, the continuous line curves relate to capsules pierced with small apertures, whereas the broken line curves relate to open capsules.

In the first case, there was a spread of the emergences over five days with about 75% of the emergences in the first 48 hours: about 48% the first day, about 27% the second day (FIG. 6) and a further 20% of the emergences from the third to the fifth day.

Figure 7:
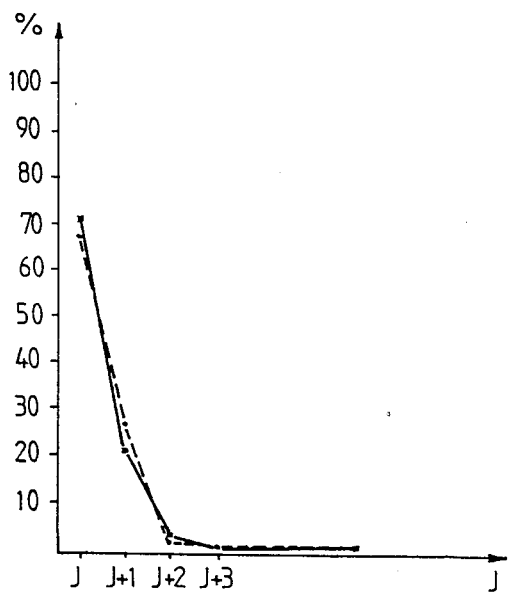

In the second case, 95% of the emergences where obtained in the first 48 hours, with about 70% the first day and 25% the second day (FIG. 7).

The parasitization method described above allows in a capsule a ratio of inoculum to healthy eggs of the host at least equal to 1/15 with superparasitization negligible, whence a substantial economy of capsule inoculum. Furthermore, the assembly of the present invention allows an automated production chain to be obtained, from the basic inoculum up to the capsule for releasing the field, said capsule being further able to produce entomophagous insects with grouped or spread emergence, while ensuring a possibility of storing conditioned elements ready for use.

As mentioned above, the capsules naturally require to be pierced so as to allow release of the emerged insects, by means for example of an automatic needle device. Pierced must however be carried out as a function of the method of use adopted, namely, either just before treatment at 10°-14° C., or after storage at 3° C. following the diapause.

The detailed description given above with respect to *trichogramma maidis* may naturally be applied to the production of another insect, since it is then sufficient to adapt the temperature and timing conditions to the biological characteristics of the individual considered.

It should moreover be understood that the present invention has only been described and shown by way of explanation and is in no wise limiting and that any useful modification may be made thereto particularly within the scope of technical equivalences without departing from its scope and spirit.

What is claimed is:

1. A device for the mass production of an entomophagous insect, comprising a multiplication cage, a first transportation belt, a second transportation belt and external means, in which host eggs are presented to an inoculum producing adult insects for parasitization of said host eggs by said adult insects, said multiplication cage forming a temperature regulated enclosure having an inlet and an outlet, said cage being provided with guide-rollers for said first transporting belt for the introduction of the inoculum and said second transporting belt for the host eggs to be parasitized; said first and second transportating belts travel through said cage along a coaxially aligned path and a motor unit for driving said first and second transporting belts;

said external means including means for recovering parasitized host eggs at said outlet, said external means also including means for reconditioning said second belt, and said external means further comprising members for forming, supporting and introducing the inoculum through said inlet.

2. The device as claimed in claim 1, wherein the rollers are formed of two coaxial rollers, one for said first belt which is narrow and carries the inoculum, the other for said belt which is wider and carries the second host eggs to be parasitized.

3. The device as claimed in claim 1, wherein the means for recovering the parasitized host eggs is formed by a brush roller receiving said second belt at the outlet of the cage, and the means for reconditioning said belt comprise a rinsing member and a member for gluing healthy hose eggs on both faces of said belt to be introduced at the inlet of the cage, the travel time of said belt outside the cage being 24 hours.

4. The device as claimed in claim 1, wherein the member for forming and supporting the inoculum is formed by a narrow belt roll disposed at the outlet of the cage and loaded with a fraction of host eggs parasitized in the cage, and the member for introducing the inoculum in the cage is formed by housing of said cage, containing five turns of said support for the inoculum, this latter having undergone previous incubation, and each intended to stay five days in the cage with renewal of a roll every 24 hours.

5. A method for the mass production of an entomophagous insect in a multiplication cage where host eggs are presented to an inoculum producing adult insects, said method comprising the steps of:
   (a) continuously introducing an inoculum of first host eggs into said cage, said first host eggs having previously been parasitized and incubated;
   (b) incubating said parasitized and previously incubated first host eggs in said cage in the presence of unparasitized second host eggs until said insects emerge from said first host eggs and parasitize said second host eggs;
   (c) collecting said parasitized second host eggs;
   (d) removing a portion of said collected parasitized second host eggs;
   (e) using said removed portion as said parasitized and previously incubated first host eggs in step (a);
   (f) cyclically repeating steps (a)–(e); and
   (g) maintaining the population of adult insects in said cage, and the temperature of said cage, essentially constant throughout steps (a)–(f).

6. The method as claimed in claim 5, wherein the entomophagous insect is *trichogramma maidis* and the host egg is that of *Ephestia kuehniella*, the temperature of said cage being 22° C., the presentation time being 24 hours and activation time of the inoculum being five days.

7. The process as claimed in claim 5, wherein said second parasitized host eggs are used as inoculum in the presence of healthy host eggs inside capsules, in the ratio of 1/15, and said capsules are subjected to a conditioning treatment relative to the parasitized and healthy eggs which are contained therein.

* * * * *